US Patent Number: 4,943,573
Date of Patent: Jul. 24, 1990

Meanwell

[54] IMIDAZO[4,5-B]QUINOLINYLOXYALK-
ANOIC ACID AMIDES WITH ENHANCED
WATER SOLUBILITY

[75] Inventor: Nicholas A. Meanwell, East Hampton, Conn.

[73] Assignee: Bristol-Myers Squibb Company, New York, N.Y.

[21] Appl. No.: 430,228

[22] Filed: Nov. 1, 1989

[51] Int. Cl.$^5$ .............. A61K 31/495; A61K 31/505; A61K 31/445; C07D 401/14; C07D 471/04
[52] U.S. Cl. .................. 514/253; 514/293; 544/295; 544/361; 546/82
[58] Field of Search ............... 544/361, 295; 546/82; 514/293, 253

[56] References Cited

U.S. PATENT DOCUMENTS

| 3,932,407 | 1/1976 | Beverung, Jr. et al. | 544/250 |
| 4,256,748 | 3/1981 | Chodnekar et al. | 514/267 |
| 4,490,371 | 12/1984 | Jones et al. | 544/250 |
| 4,668,686 | 5/1987 | Meanwell et al. | 546/82 |
| 4,701,459 | 10/1987 | Meanwell et al. | 546/82 |
| 4,775,674 | 10/1988 | Meanwell et al. | 544/361 |

FOREIGN PATENT DOCUMENTS 153152 8/1985 European Pat. Off. .

OTHER PUBLICATIONS

Kozak et al., Bull. Intern. Acad. Polanaise, 1930A, 432–438, (Chem. Abst., 25, 5400 is provided).
J. S. Fleming et al., New Drugs, Annual: Cardiovascular Drugs, Raven Press, pp. 277–294, (1983).
Fried et al., Chem. Abst., 104—34338x, (1986), eq. EP-153152.
Musial; Roczniki Chem., 1951, 25; 46–52, (Chem. Abst., 1953, 47, 4885f is provided).
Ried et al., Chem. Ber., 1956, 89, 2684–2687.

Primary Examiner—Cecilia Shen
Attorney, Agent, or Firm—Robert H. Uloth

[57] ABSTRACT

A novel series of 2,3-dihydro-2-oxo-1H-imidazo[4,5-b]quinolinyloxyalkanoic acid amides having enhanced water solubility is disclosed of the formula

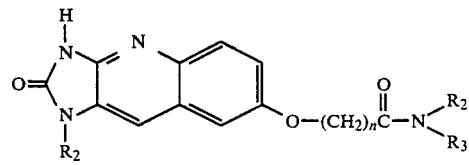

wherein n is 3 to 5; $R_1$ is alkyl of 1 to 4 carbon atoms; $R_2$ is hydrogen; $R_3$ is 1-piperidinylethyl, 1-benzylpiperidin-4-yl, 4-(1-piperidinyl)piperidine, (1-alkyl-2-pyrrolidinyl)alkyl where alkyl is 1 to 4 carbon atoms, 3-quinuclidinyl; $R_2$ and $R_3$ together with the nitrogen atom to which they are attached form 4-$R_4$-piperazin-1-yl wherein $R_4$ is alkyl of 1 to 7 carbon atoms, alkoxyethyl of 3 to 7 carbon atoms, pyridinyl, pyrimidinyl, tetrahydropyranylmethyl, thienylmethyl, cycloalkyl-$(CH_2)_m$ where m is zero or one and cycloalkyl is 5 to 7 carbon atoms except m is zero when cycloalkyl is 7 carbon atoms, benzyl, 4-fluorobenzyl, 3-trifluoromethylbenzyl, 4-alkoxybenzyl where alkoxy is 1 to 4 carbon atoms.

The compounds are cyclic AMP phosphodiesterase inhibitors and are particularly useful as inhibitors of blood platelet aggregation and/or as cardiotonic agents.

37 Claims, No Drawings

IMIDAZO[4,5-B]QUINOLINYLOXYALKANOIC ACID AMIDES WITH ENHANCED WATER SOLUBILITY

BACKGROUND OF THE INVENTION

This invention generally pertains to heterocyclic carbon compounds having drug and bio-affecting properties and to their preparation and use. In particular, the invention is concerned with a series of new 2,3-dihydro-2-oxo-1H-imidazo[4,5-b]quinolinyloxyalkanoic acid amides wherein a basic nitrogen atom is incorporated in the amide grouping. The alkanoic amide derivatives are phosphodiesterase inhibitors, blood platelet antiaggregators and cardiotonic agents.

The heterocycle "2,3-dihydro-2-oxo-1H-imidazo[4,5-b]quinoline" of formula (1), alternately referred to as 1,3-dihydro-2H-imidazo[4,5-b]quinolin-2-one, was described by Kozak, et al., *Bull. Intern. Acad. Polanaise,* 1930A, 432–438 (Chem. Abs. 25, 5400)

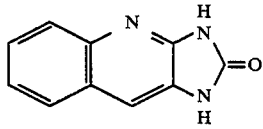

(1)

Derivatives of formula (1) having cyclic AMP phosphodiesterase inhibitory activity have been prepared and studied for their platelet inhibition and cardiotonic properties. Thus, for example:

Meanwell, et al., U.S. Pat. No. 4,775,674 describe a series of 2,3-dihydro-2-oxo-1H-imidazo[4,5-b]quinolinyl ether derivatives of formula (2)

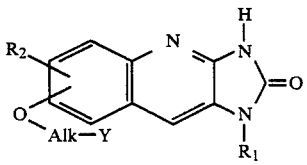

(2)

wherein $R_1$ is hydrogen, lower alkyl, benzyl $R_2$ is hydrogen, halogen, lower alkyl lower alkoxy; Alk is alkylene; Y is hydroxy and alkanoic or aralkanoic esters thereof, oxo ketone, dialkylamino, carboxylic acid and esters, carboxamides, alkoxy, ethanolamines and cyclic carbamates thereof, tetrazolyl, and optionally substituted phenylsulfonyl.

Meanwell et al., U.S. Pat. No. 4,701,459 describe another series of 2,3-dihydro-2-oxo-1H-imidazo-[4,5-b]quinoline compounds comprising amine derivatives of formula (3)

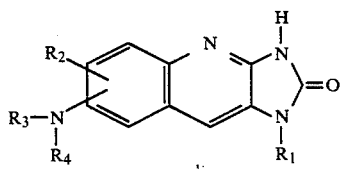

(3)

wherein $R_1$ is hydrogen, lower alkyl; $R_2$ is hydrogen, lower alkyl, lower alkoxy, halogen; $R_3$ is hydrogen, lower alkyl; $R_4$ is hydrogen, lower alkyl, alkanoyl, phenylalkanoyl wherein phenyl is optionally substituted with halogen, lower alkyl, lower alkoxy, $R_3$ and $R_4$ are joined together to form morpholinyl, piperidinyl or pyrrolidinyl optionally substituted with $-CO_2R_5$ or

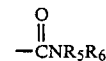

$-CNR_5R_6$ wherein $R_5$ is hydrogen or lower alkyl, and $R_6$ is hydrogen, lower alkyl, cycloalkyl; 4-$R_7$-piperazinyl wherein $R_7$ is $-CO_2R_8$ wherein $R_8$ is lower alkyl, phenyl optionally substituted with up to 2 halogen, lower alkyl or lower alkoxy: phenylalkanoyl of 7 to 10 carbon wherein phenyl is unsubstituted or independently substituted with up to 2 halogen, lower alkyl, lower alkoxy.

Meanwell, et al., U.S. Pat. No. 4,668,686 describe still another series of 1,3-dihydro-2H-imidazo-[4,5-b]quinolin-2-ones comprising derivatives of formula (4)

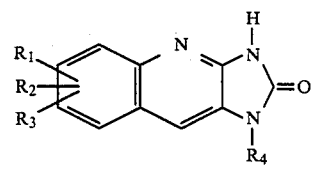

(4)

wherein $R_1$ is halogen, lower alkyl, lower alkoxy, trifluoromethyl; $R_2$ is hydrogen, halogen, lower alkyl, lower alkoxy; $R_3$ is hydrogen, halogen, lower alkyl, lower alkoxy; and $R_4$ is hydrogen or lower alkyl.

Another class of heterocyclic compounds having phosphodiesterase inhibiting and anti-platelet aggregation activity comprise the tetrahydroimidazo[2,1-b]quinazolin-2-ones of formula (5).

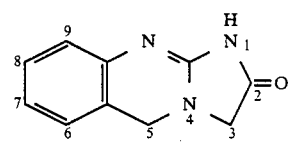

(5)

For example:

Beverung, Jr., et al., U.S. Pat. No. 3,932,407 disclose a series of compounds useful as blood platelet antiaggregative and/or antihypertensive and/or bronchodilator agents of the tetrahydroimidazo[2,1-b]- quinazolin-2-one class. Anagrelide (6), a particularly preferred member of the Beverung, Jr., et al. series, has been studied extensively, e.g., J. S. Fleming, *et al., New Drugs Annual: Cardiovascular Drugs,* Raven Press, pages 277–294, New York (1983).

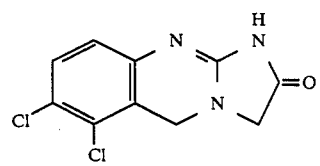

(6)

Chodnekar, et al., U.S. Pat. No. 4,256,748 describe a series of tetrahydroimidazo[2,1-b]quinazolin-2-ones of the formula (7) as inhibitors of the aggregation of blood platelets and cardiotonic activity.

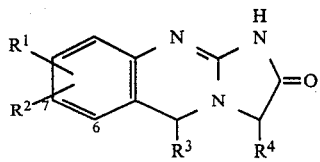

(7)

Representative of the Chodneker compounds are RO 15-2041 ($R^4$=CH$_3$, $R^3$=H, $R^2$=6-CH$_3$, $R^1$=7-Br) and RO 13-6438 ($R^4$=CH$_3$, $R^3$=H, $R^2$=6-CH$_3$, $R^1$=H).

Jones, et al., U.S. 4,490,371 describe another series of tetrahydroimidazo[2,1-b]quinazolin-2-one derivatives as cyclic AMP phosphodiesterase inhibitors useful as thrombogenic agents. Among the compounds disclosed is the formula (8) amide, identified in the art as RS82856.

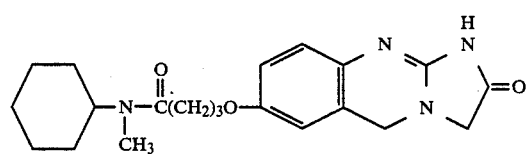

(8)

Jones, et al., European Patent Application 153152 further describe tetrahydroimidazo[2,1-b]quinazolin-2-ones of formula (9) as cyclic AMP phosphodiesterase inhibitors useful as antithrombogenic agents.

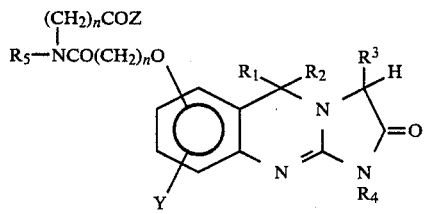

(9)

Compounds of the aforementioned patents generally display limited solubility in water, acidic or alkali media and common organic solvents. For instance, the formula (2) compound "1-[4-[(2,3-dihydro-2-oxo-1H-imidazo[4,5-b]- quinolin-7-yl)oxy]-1-oxobutyl]-4-phenylpiperazine" has a solubility of less than 0.01 milligrams per milliliter of water or 2.0N HCl.

SUMMARY OF THE INVENTION

In its broadest aspect, this invention is concerned with a new series of 2,3-dihydro-2-oxo-1H-imidazo-[4,5-b]quinoline derivatives incorporating an 7-oxyalkanoic acid amide side chain wherein the amide grouping has a basic nitrogen in addition to the amide nitrogen. These compounds have enhanced water solubility compared to the formula (2) quinolinyl ether derivatives. Formula I illustrates the compounds of the invention and the ring numbering system used herein.

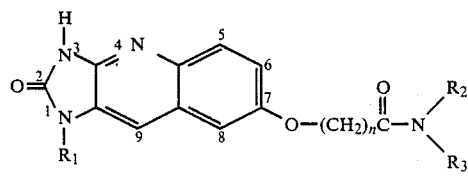

(I)

In the foregoing formula:

n is 3 to 5:
$R_1$ is alkyl of 1 to 4 carbon atoms:
$R_2$ is hydrogen;
$R_3$ is 1-piperidinylethyl, 1-benzylpiperidin-4-yl, 4-(1-piperidinyl)piperidine, (1-alkyl-2-pyrrolidinyl)alkyl where alkyl is 1 to 4 carbon atoms, 3-quinuclidinyl;
$R_2$ and $R_3$ together with the nitrogen atom to which they are attached form 4-$R_4$-piperazin-1-yl wherein $R_4$ is alkyl of 1 to 7 carbon atoms, alkoxyethyl of 3 to 7 carbon atoms, pyridinyl, pyrimidinyl, tetrahydropyranylmethyl, thienylmethyl, cycloalkyl-(CH$_2$)m where m is zero or one and cycloalkyl is 5 to 7 carbon atoms except m is zero when cycloalkyl is 7 carbon atoms, benzyl, 4-fluorobenzyl, 3-trifluoromethylbenzyl, 4-alkoxybenzyl where alkoxy is 1 to 4 carbon atoms.

Another embodiment of the invention relates to pharmaceutically acceptable compositions comprised of a Formula I compound combined with at least one pharmaceutically acceptable excipient. A further embodiment of this invention relates to a method for inhibiting phosphodiesterase and blood platelet aggregation in a mammal which comprises administering a therapeutically effective amount of a compound of Formula I or a pharmaceutically acceptable salt thereof to a mammal in need of such treatment. A still further embodiment of this invention relates to a method for increasing heart inotropic activity which comprises administering a therapeutically effective amount of a compound of Formula I or a pharmaceutically acceptable salt thereof to a mammal in need of such treatment.

DETAILED DESCRIPTION OF THE INVENTION

The compounds of the instant invention comprise those of Formula I

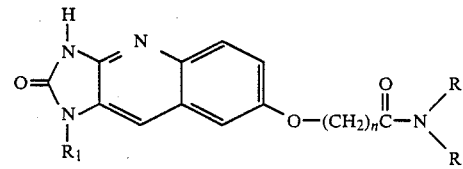

(I)

wherein
n is 3 to 5;
$R_1$ is alkyl of 1 to 4 carbon atoms;
$R_2$ is hydrogen;
$R_3$ is 1-piperidinylethyl, 1-benzylpiperidin-4-yl, 4-(1-piperidinyl)piperidine, (1-alkyl-2pyrrolidinyl)alkyl where alkyl is 1 to 4 carbon atoms, 3-quinuclidinyl:
$R_2$ and $R_3$ together with the nitrogen atom to which they are attached form 4-$R_4$-piperazin-1-yl wherein $R_4$ is alkyl of 1 to 7 carbon atoms, alkoxyethyl of 3 to 7 carbon atoms, pyridinyl, pyrimidinyl, tetrahydropyranylmethyl, thienylmethyl, cycloalkyl-(CH$_2$)$_m$ where m is zero or one and cycloalkyl is 5 to 7 carbon atoms except m is zero when cycloalkyl is 7 carbon atoms, benzyl, 4-fluorobenzyl, 3-trifluoromethylbenzyl, 4-alkoxybenzyl where alkoxy is 1 to 4 carbon atoms:
or a pharmaceutically acceptable salt thereof.

It is understood that as used herein limitations of Formula I are further defined as follows:

The term "alkyl" refers to a branched or unbranched saturated hydrocarbon chain containing the designated number of carbon atoms. For example, where alkyl is 1 to 4 carbon atoms, the groups methyl, ethyl, n-propyl, isopropyl, n-butyl, secondary butyl and tert.-butyl are included. The terms "alkyl of 1 to 4 carbon atoms" and "lower alkyl" are used interchangeably and specific terms may be represented by conventional symbols, i.e., Me=CH, Et=C$_2$H$_5$, etc.

The term "alkoxy" comprehends ethers of the designated number of carbon atoms. For example, alkoxy of 1 to 4 carbon atoms refers to methoxy, ethoxy, isopropoxy, and tert.-butoxy.

According to the present invention, the compounds characterized by Formula I and the pharmaceutically acceptable acid addition salts thereof are obtained by a process comprising (a) coupling a carboxylic acid of Formula II

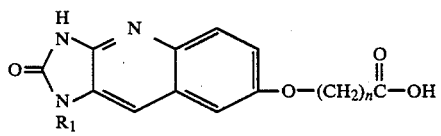

wherein R$_1$ is lower alkyl and n is 3 to 5 with an amine of Formula III:

wherein

R$_2$ is hydrogen:

R$_3$ is 1-piperidinylethyl, 1-benzylpiperidin-4-yl, 4-(1-piperidinyl)piperidine, (1-alkyl-2-pyrrolidinyl)alkyl where alkyl is 1 to 4 carbon atoms, 3-quinuclidinyl:

R$_2$ and R$_3$ together with the nitrogen atom to which they are attached form 4-R$_4$-piperazin-1-yl wherein R$_4$ is alkyl of 1 to 7 carbon atoms, alkoxyethyl of 3 to 7 carbon atoms, pyridinyl, pyrimidinyl, tetrahydropyranylmethyl, thienylmethyl, cycloalkyl-(CH2)$_m$ where m is zero or one and cycloalkyl is 5 to 7 carbon atoms except m is zero when cycloalkyl is 7 carbon atoms, benzyl, 4-fluorobenzyl, 3-trifluoromethylbenzyl, 4-alkoxybenzyl where alkoxy is 1 to 4 carbon atoms;

(b) converting the free base of a compound of Formula I to a pharmaceutically acceptable salt when desired.

Conventional acylation methods for coupling a carboxylic acid and an amine are employed such as reacting a methyl ester of II with III.

The Formula III amines were obtained from commercial sources or synthesized from N-formyl piperzine as depicted below. Thus, N-formyl piperazine (V) was alkylated with IV and the substituted piperazine (VI) then hydrolyzed to provide the mono alkylated piperazine intermediate III.

The alkyl halides in turn were commercially available or synthesized from the corresponding alcohol by exposure to thionyl chloride.

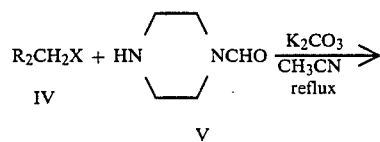

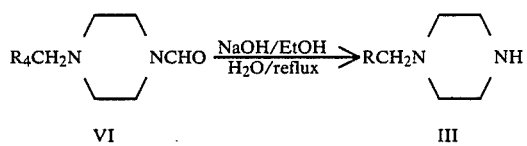

A preferred method for coupling carboxylic acid II and amine III consists of using diphenylphosphoryl azide in dimethylformamide (DMF) in the presence of a catalytic quantity of 4-dimethylaminopyridine and two to four molar equivalent of an organic base such as triethylamine. In general, the Formula I amides separate from the reaction medium upon stirring and are isolated by diluting the reaction mixture with water and filtering off the product. Amides soluble in DMF are precipitated by the addition of water and collected by filtration. Purification of the Formula I products is effected by recrystallization from aqueous DMF.

Conventional methods are used in converting the free base of a compound of Formula I to a salt. For instance, pharmaceutically acceptable salts of Formula I are obtained by treating a Formula I base with the selected acid preferably in methanol. They may also be made by metathesis or treatment with an ion exchange resin under conditions in which the anion of one salt of the substance of the Formula I is replaced by another anion under conditions which allow for separation of the desired species such as by precipitation from solution or extraction into a solvent, or elution from one retention of an ion exchange resin. The pharmaceutically acceptable acid addition salts of the instant invention are those in which the anion does not contribute significantly to the toxicity or pharmacological activity of the salt and, as such, they are the pharmacological equivalents of the bases of Formula I. In some instances, physical properties which make them more desirable for pharmaceutical formulation purposes such as solubility lack of hygroscopicity, compressibility with respect to tablet formation and compatibility with other ingredients with which the substance may be used for pharmaceutical purposes. Pharmaceutically acceptable acids for the purposes of salt formation of the substances of Formula I include hydrochloric, hydrobromic, hydroiodic, citric, acetic, propionic, benzoic, mandelic, sulfuric, phosphoric, nitric, mucic, isethionic, methanesulfonic, ethanesulfonic, p-toluene sulfonic, palmitic, heptanoic, and others.

The Formula I hydrochloride salts have enhanced aqueous solubility relative to the Meanwell, et al. U.S. Pat. No. 4,775,674 quinolinyl ether derivatives of formula (2). For example, hydrochloride salts of Formula I compounds are generally soluble at concentrations of greater than 10 milligrams per milliliter in contrast to the formula (2) quinolinylethers which are essentially insoluble.

As stated above, the Formula I compounds or pharmaceutically acceptable salts thereof have pharmacological properties which make them particularly useful as phosphodiesterase inhibitors, blood platelet antiaggregators and/or cardiotonic agents. Regarding the latter, compounds of the invention selectively strengthen myocardial contraction force by which the heart ventricles pump blood into the periphery. Thus, the instant compounds are useful in the curative or prophylactic treatment of cardiac conditions such as myocardial failure where an increase in positive inotropic activity is desirable. Preferred compounds increase contractile force without unduly increasing heart rate.

Platelet aggregation is considered part of a complex physiological mechanism for formation of a thrombus in the vascular system. Thromboembolic phenomena, i.e., the formation of thrombi, are involved in hemostasis and a number of diseased states in mammals including thrombophlebitis, phlebothrombosis, cerebral thrombosis, coronary thrombosis and retinal vessel thrombosis. An increase in propensity for platelet aggregation, sometimes referred to as platelet adhesiveness, is observed following parturition, surgical operations such as coronary artery bypass surgery, organ transplant, angioplasty, prosthetic heart valve implants to name a few; and in ischaemic heart disease, atheroscloeris, multiple sclerosis, intracranial tumors, thromboembolism, and hyperlipemia: refer to A. Poplawski, et al., *J. Atherosclerosis Research*, 8, 721 (1968). Thus, the compounds of the invention which have antithrombogenic (inhibit blood platelet aggregation) and phosphodiesterase inhibition properties are useful in prevention or treatment of conditions involving platelet aggregation and thrombosis such as the above. Literature relating to prophylactic and therapeutic activities of phosphodiesterase inhibiting compounds include the following: S. M. Amer, "Cyclic Nucleotides as Targets for Drug Design,"*Advances in Drug Research*, Vol. 12, 1977, Academic Press, London, pp 1-38: I. Weinryh, et al., *J. Pharm. Sci.*, pp 1556-1567 (1972): S. M. Amer, et al., *J. Pharm. Sci.*, Vol. 64, pp 1-37 (1975); and D. N. Harris, et al., *Enzyme Inhibitors As Drugs*, McMillan & Co., Ed. M. Standler, pp 127-146 (1980). The instant compounds are considered to have antimetastatic potential in view of their platelet inhibition properties.

The pharmacological properties of the instant compounds can be demonstrated by conventional in vitro and in vivo biological tests such as the following.

IN VITRO INHIBITION OF PLATELET AGGREGATION

The aggregometer method of Born[1], as modified by Mustard, et al.[2] was used to assess the in vitro activity of the various compounds as to inhibition of adenosine diphosphate (ADP) and collagen-induced platelet aggregation. Platelet rich plasma (PRP) was separated by centrifugation from citrated (3.8 percent) human blood. ADP in final concentration of 2.5 mcg/ml or 0.05 ml of a collagen suspension prepared according to the method described by Evans, et al.[3] was used to induce aggregation. The various compounds tested were dissolved in dimethylsulfoxide (DMSO) so that 5 mcl added to the platelet rich plasma would yield the desired test concentration. Vehicle control trials were done and compared with aggregation induced in platelet rich plasma containing various concentrations of the test compounds. Dose response curves were thus obtained and Effective Concentration ($EC_{50}$) values calculated.

1. Born, G. V. R., J. Physiol., London, 162, 67P (1962).
2. Mustard, J.F., Hegardt, B., Rowsell, H.C. and MacMillan, R.L., J. Lab. Clin. Med., 64, 548 (1964).
3. Evans, G., Marian, M.C., Packham, M.A., Nishizawa, E.E., Mustard, J.F. and Mruphy, E.A., J. Exp. Med., 128, 877 (1968).

With respect to inhibition of ADP-induced platelet aggregation, $EC_{50}$ values for Formula I compounds vary within the range of $6 \times 10^{-8}$ to $8 \times 10^{-5}$ molar. The $EC_{50}$ value versus ADP for a preferred compound "1-(cyclohexylmethyl)-4-[4-(2,3-dihydro-2-oxo-1H-imidazo-[4,5-b]quinolin-7-yloxy)-1-oxobutyl]piperazine" as the dihydrochloride salt is $9.1 \times 10^{-7}$ molar.

INHIBITION OF CYCLIC AMP PHOSPHODIESTERASE

This assay is carried out essentially as described by Thompson, et al., *Methods in Enzymology*, 38, 205-121 (1974). Briefly, tritium labeled cyclic adenosine monophosphate (cAMP) is incubated with a phosphodiesterase (PDE) enzyme obtained from human platelets which converts a portion of the cAMP to 5'AMP in culture tubes. This reaction is terminated by submerging the tubes in a boiling water bath after which they are placed on ice and an aliquot of snake venom is added to each tube. This, during a second incubation, converts the 5'AMP to adenosine. Ion exchange resin is added to bind the remaining cyclic AMP. The tubes are centrifuged to sediment the resin and a portion of the clear supernatent (which contains radioactive adenosine) is counted in a liquid scintillation counter. The cAMP phosphodiesterase inhibition activity of a test agent is determined by pre-incubating the PDE enzyme preparation with the test agent. Dose response values are obtained and activity of the test agent reported as the molar (M) concentration of the test agent inhibition 50% of the PDE activity ($IC_{50}$s). In this test, the $IC_{50}$ value of milrinone, a known inotropic agent, is $2 \times 10^{-7}$ molar. Theophylline, another standard phosphodiesterase inhibitor, has an $IC_{50}$ value of $1 \times 10^{-4}$ molar.

In general, the compounds of Formula I exhibit potent inhibitory cAMP effects within the range of $10^{-8}$ and $10^{-10}$ molar. For example, "1-(cyclohexylmethyl)-4-[4-(2,3-dihydro-2-oxo-1H-imidazo[4,5-b]quinolin-7-yloxy)-1-oxobutyl]piperazine" has an $IC_{50}$ of $4 \times 10^{-10}$ molar.

IN VIVO INOTROPIC ACTIVITY

This test is carred out in ferrets as follows.

Fasted anesthetized ferrets are instrumented to study hemodynamic parameters as well as right ventricular contractile force (RVCF) using a Walton-Brodie open strain gauge arch. Drugs are administered intraduodenally as solutions in DMSO (1 mL or less) and effects on myocardial contractile force and other parameters are monitored for 60 minutes after dosing. Changes in contractile force in response to drug treatment are expressed in terms of percent change from predose control.

In this test, milrinone produces a 52% increase in RVCF at 3 mg/kg. Results are given in Table I for various Formula I compounds tested in the "Biolaser Model" described below.

IN VIVO INHIBITION OF BIOLASER-INDUCED PLATELET AGGREGATION IN THE RABBIT EAR

Transparent ear chambers were chronically implanted in adult, English, half-lop rabbits. The animals were conditioned to lie quietly in a supine position. Localized microvascular injury was induced by focusing a single pulse ruby laser beam through a microscope into the lumen of a vessel 10-30 $\mu M$ in diameter. This evoked the formation of a small thrombus consisting of platelets accumulated around a core of one or two damaged red cells. Thrombi areas were determined using computerized planimetry. The mean thrombus area (μM²) obtained for 10 trials in each rabbit served as the control value. Subsequently, the test compound was administered orally and 2 hours later a second series of laser-induced thrombi trials were performed. Drug activity was evaluated by comparing pre-and post-dose mean thrombus areas. Activity determined at other time points beyond 2 hours establish duration of action.

Results for various Formula I compounds tested in this model are given in Table I along with the PDE inhibitory and Ferret inotropic values.

TABLE I

Inhibition of cAMP Phosphodiesterase, Inotropic and Hemodynamic Effects and Inhibition of Biolaser-Induced Thrombosis

| Example[a] | cAMP PDE IC$_{50}$ (m) | Ferret, 3 mg/kg Maximum % Change | | | Biolaser 0.1 mg/kg Inhibition |
|---|---|---|---|---|---|
| | | VCF[b] | MAP[c] | HR[d] | |
| 11 | 7 × 10$^{-10}$ | +28 | −42 | +31 | 50% |
| 19 | 5 × 10$^{-9}$ | −8 | −15 | +12 | 47% |
| 25 | 9 × 10$^{-10}$ | +26 | −12 | +17 | 49% |
| 13 | 2 × 10$^{-9}$ | +32 | −11 | +21 | 46% |
| 14 | 9 × 10$^{-9}$ | +3 | −16 | +12 | 49% |
| 15 | 3 × 10$^{-9}$ | +24 | −23 | +17 | 48% |
| 22 | 4 × 10$^{-10}$ | +27 | −15 | +29 | 59% |
| 16 | 7 × 10$^{-10}$ | +30 | −27 | +16 | 49% |

[a]Refer to examples below for compound identification.
[b]Ventricular contractile force.
[c]Mean arterial blood pressure.
[d]Heart rate.

In the Biolaser Model, the formula (2) compound "1-[4-[(2,3-dihydro-2-oxo-1H-imidazo[4,5-b]quinolin-7-yl)oxy]-1-oxobutyl]-4-phenylpiperazine" of Meanwell, et al. U.S. Pat. No. 4,775,674 was markedly less active than Table I compounds providing 22% inhibition at a dose of 0.3 mg/kg body weight.

The dosage employed in the instant therapeutic methods will vary with the form of administration, the particular compound chosen, the subject being tested and the effect desired. Suitable effective doses in animals range from 0.5–30 mg/kg body weight orally and from 0.05–10 mg/kg body weight parenterally (generally characterized as subcutaneous, intramuscular, and intravenous injection). It is contemplated that the effective unit dose in man will range from 0.1 to 30 mg. and preferably from 0.5 to 20 mg. administered one to three times a day. In accordance with conventional clinical practice, the effective dose can be determined by administering a Formula I compound at a dosage substantially less than the dose of the compound which is thought to be effective and then increasing the dosage in small increments until the desired effect is achieved.

In carrying out the instant therapeutic methods, the active ingredient of Formula I and pharmaeutically acceptable acid addition salts thereof are preferably administered with a pharmaceutically acceptable carrier and such compositions constitute part of the instant invention. Suitable dosage forms for oral use are tablets, dispersible powders, granules, capsules, syrups and elixirs. Examples of parenteral forms are solutions, suspensions, dispersions, emulsions, and the like. The compositions for oral use may contain one or more conventional adjuvants, such as sweetening agents, flavoring agents, coloring agents and preserving agents, in order to provide a composition of suitable pharmaceutical elegance. Tablets may contain the active ingredient in admixture with conventional pharmaceutical acceptable excipients including inert diluents such as calcium carbonate, sodium carbonate, lactose and talc: granulating and disintegrating agents such as starch and alginic acid; binding agents such as starch, gelatin and acacia and lubricating agents such as magnesium stearate, stearic acid and talc. The tablets may be uncoated or coated by known techniques to delay disintegration and absorption in the gastrointestinal tract and thereby provide a sustained action over a longer period. Similarly, suspension, syrups and elixirs may contain the active ingredient in admixture with any of the conventional excipients utilized for the preparation of such compositions such as suspending agents (e.g., methylcellulose, tragacanth, and sodium alginate), wetting agents (e.g., lecithin, polyoxyethylene stearate) and preservatives such as ethyl-p-hydroxybenzoate. Capsules may contain the active ingredient alone or admixed with an inert solid diluent such as calcium carbonate, calcium phosphate and kaolin. The injectible compositions are formulated as known in the art and may contain appropriate dispersing or wetting agents and suspending agents identical or similar to those mentioned above.

The following examples are given by way of illustration and are not to be construed as limiting the invention in any way inasmuch as many variations of the invention are possible within the spirit of the invention. All temperatures are degrees centrigrade and melting points taken with a Thomas Hoover capillary apparatus are uncorrected. Conventional abbreviations are employed in reporting Nuclear Magnetic Resonance (NMR) spectral data with tetramethylsilane as internal reference and chemical shift data values in parts per million. In the structural depiction of the compounds of the invention, the heterocyclic radical "2,3-dihydro-2-oxo-1H-imidazo[4,5-b]quinolin-7-yl" is represented as follows.

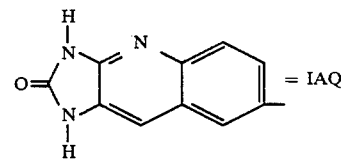

EXAMPLE 1

4-[2,3-Dihydro-2-oxo-1H-imidazo[4,5-b]quinolin-7-yl)oxy]-N-[2-(1-piperidinyl)ethyl]butanamide

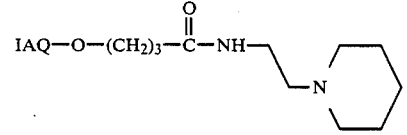

A mixture of 1-(2-aminoethyl)piperidine (1.10 g, 1.23 mL, 8.6 mmol) and methyl 4-[2,3-dihydro-2-oxo-1H-imidazo[4,5-b]quinolin-7-yl)oxy]butanoate (2 g, 6.6 mmol) was heated with stirring at 200° C. under an atmosphere of nitrogen. Additional portions of 1-(2-aminoethyl)piperidine (1.10 g, 1.23 mL, 8.6 mmol) were added after 5 minutes and again after 30 minutes. After stirring for an additional 75 minutes at 200° C., the cooled crude free base product was dissolved in methanol by adding an excess of a 10% solution of hydrogen chloride in ethanol. The solvent was evaporated and the residue triturated in a mixture of methanol and diethyl ether. Solids were collected (yield 79%) and crystallized from isopropanol to afford 4-[(2,3-dihydro2-oxo-1H-imidazo[4,5-b]quinolin-7-yl)oxy]-N-[2-(1- piperidinyl)ethyl]butanamide as the dihydrochloride salt, 2.47 g, m.p. indistinct (decomposed at 200°).

Anal. Calcd. for $C_{21}H_{27}N_5O_3 \cdot 2HCl$: C, 53.62: H, 6.21;, N, 14.89. Found: C: 54.16; H, 6.28; N, 14.76%.

$^1$H-NMR (DMSO) delta 1.20 to 1.40 (1H,m) and 1.60 to 1.90 (5H,m), 1.98 (2H, t, J=7 Hz), 2.31 (2H, t, J=7 Hz), 2.82 (2H, m), 3.05 (2H, m), 3.30 to 3.60 (4H, m), 4.02 (2H, t, J=6 Hz), 7.18 (1H, dd, J=9 Hz, J$^1$=2.5 Hz), 7.38 (1H, d, J=2.5 Hz), 7.66 (1H, s), 7.78 (1H, d, J=9 Hz), 7.00 to 8.00 (1H, bs), 8.44 (1H, t, J=5 Hz), 10.63 (1H, bs), 11.40 (1H, s).

EXAMPLE 2

4-[(2,3-Dihydro-2-oxo-1H-imidazo[4,5-b]quinolin7-yl)oxy]-N-[(1-ethyl-2-pyrrolidinyl)methyl]butanamide

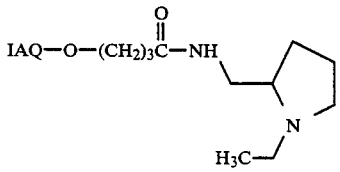

Prepared by reacting 2-(1-ethyl-2-pyrrolidinyl)-ethylamine and methyl 4-[2,3-dihydro-2-oxo-1H-imidazo[4,5-b]quinolin-7yl)oxy]butanoate (2g) analogously to the procedure of Example 1. Crystallization of the crude free base from aqueous dimethylformamide provided the title product, 1.70 g (65% yield), m.p. 233°–237° C.

Anal. Calcd. for $C_{21}H_{27}N_5O_3$: C, 63.46; H, 6.85; N, 17.62%. Found: C, 65.50; H, 6.69; N, 18.05%.

$^1$H-NMR (DMSO) delta 0.98 (3H, t, J=7 Hz), 1.35 to 1.95 (4H, m), 1.97 (2H, t, J=7 Hz), 2.00 to 2.60 (3H, m), 2.28 (2H, t, J=7 Hz), 2.65 to 3.05 (3H, m), 3.25 (1H, m), 4.01 (2H, t, J=6 Hz), 7.11 (2H, dd, J=9 Hz J$^1$=2.5 Hz), 7.28 (1H, d, J=2.5 Hz), 7.48 (1H, s), 7.65 (1H, d, J=9 Hz), 7.93 (1H, bs), 10.97 (1H, bs) and 11.35 (1H, bs).

EXAMPLE 3

4-[2,3-Dihydro-2-oxo-1H-imidazo-[4,5-b]quinolin-7-yl)oxo]-N-[2-(1-methyl-2-pyrrolidinyl)ethyl]butanamide

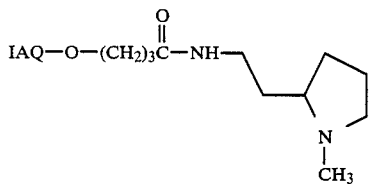

Prepared by reacting 2-(1-methyl-2-pyrrolidinyl)ethylamine and methyl 4-[2,3-dihydro-2-oxo-1H-imidazo[4,5-b]quinolin-7-yl)oxy]butanoate (2 g) analogously to the procedure of Example 1. Crystallization of the crude free base from aqueous dimethylformamide provided the title product as a partial hydrate, 1.83 g (70% yield), m.p. 248°–251° C.

Anal. Calcd. for $C_{21}H_{27}N_5O_3 \cdot 0.2H_2O$: C, 62.89: H, 6.89; N, 17.47: H$_2$O, 0.90%. Found: C, 61.51; H, 6.46; N, 16.92: H$_2$O, 0.67%.

$^1$H NMR (DMSO) delta 1.22 (2H, m), 1.51 (2H, m), 1.60 to 2.00 (5H, m), 2.13 (3H, s), 2.25 (2H, t, J=7 Hz), 2.86 (1H, m), 3.03 (2H, m), 4.00 (2H, t, J=6 Hz), 7.11 (1H, dd, J=9Hz, J$^1$=2.5 Hz), 7.48 (1H), 7.64 (1H, d, J=9 Hz), 7.85 (1H, t, J=5 Hz), 7.28 (1H, d, J=2.5 Hz), 10.99 (1H, bs), and 11.36 (1H, bs).

EXAMPLE 4

4-(2,3-Dihydro-1-oxo-1H-imidazo[4,5-b]-quinolin-7-yloxy)-N-[1-(phenylmethyl)-4-piperidinyl)butanamide

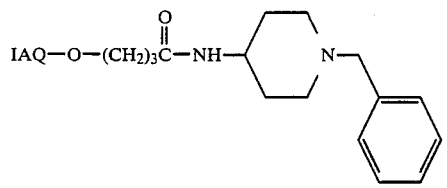

A mixture of 4-[(2,3-dihydro-2-oxo-1H-imidazo-[4,5-b]quinolin-7-yl)oxy]butyric acid (2 g, 7mmol), 4-amino-1-benzylpiperidine (1.59 g, 1.70 mL, 8.4 mmol), triethylamine (1.54 g, 2.12 mL, 15.2 mmol), diphenylphosphoryl azide (2.87 g, 2.25 mL, 10.4 mmol), 4-dimethylaminopyridine (catalytic quantity) and dimethylformamide (40 mL) was stirred at room temperature for 18 hours. The mixture was then diluted with water and the crude free base product collected. After air drying, the free base was suspended in methanol and acidified with a 10% solution of hydrogen chloride in ethanol. The solution was evaporated and the residue dissolved in methanol. Dilution of the methanol solution with diethyl ether gave 4-(2,3-dihydro-2-oxo-1H-imidazo[4,5-b]quinolin-7-yloxy)-N-[1-(phenylmethyl)-4-piperidinyl]butanamide as the hydrated dihydrochloride salt (3.00 g, 80%), mp. 202°–204 C.

Anal Calcd. for $C_{26}H_{29}N_5O_3 \cdot 2HCl \cdot 0.4H_2O$: C, 57.87: H, 5.94; N, 12.98: H$_2$O, 1.34. Found: C, 58.16: H, 6.22; N, 13.05: H$_2$O, 1.62%.

$^1$H-NMR (DMSO-d$^6$) delta 1.65 to 2.10 (6H, m), 2.25 and 2.38 (2H, triplets, J=6 Hz), 3.00 (2H, m), 3.30 (2H, m), 3.72 (1H, m), 3.99 (2H, t, J=6 5 Hz), 4.21 (2H, m), 7.16 (1H, dd, J=9 Hz, J$^1$=2.5 Hz), 7.38 (4H, m), 7.68 (3H, m), 7.79 (1H, d, J=9 Hz), 8.17 and 8.44 (1H, two doublets, J=7 Hz), 11.20 (1H, bs), 11.45 (1H, s), 11.90 (1H, bs).

EXAMPLE 5

N-(1-Azabicyclo[2.2.2]oct-3-yl)-4-[2,3-dihydro-2-oxo-1H-imidazo[4,5-b]-quinolin-7-yl)oxy]butanamide

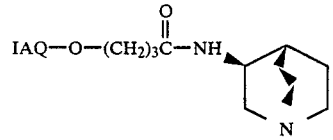

A mixture of 4-[2,3-dihydro-2-oxo-1H-imidazo-[4,5-b]quinolin-7-yl)oxy]butyric acid (2 g, 7mmol), 3-aminoquinuclidine dihydrochloride (1.66 g, 8.3 mmol), triethylamine (2.95 g, 4.05 mL, 29 mmol), diphenylphosphoryl azide (2.87 g, 2.25 mL, 10.4 mmol), 4-dimethylaminopyridine (catalytic quantity) and dimethylformamide (40 mL) was stirred at room temperature for 54 hours. The mixture was then diluted with water and insolubles collected. This material (2.2 g after air drying) was suspended in methanol and acidified with a 10% solution of hydrogen chloride in ethanol. The solution was evaporated and the residue triturated with a mixture of ethanol and diethyl ether to give N-(1- azabicyclo[1.1.1]oct-3-yl)-4-[2,3-dihydro-2-oxo-1H-imidazo[4,5-b]quinolin-7yl)oxy)butanamide as the dihydrochloride salt, 2.34 g (71%), mp 242°–245° C.

Anal. Calcd. for C$_{22}$H$_{25}$N$_5$O$_3$.2HCl: C, 53.85; H, 5.81; N, 14.95. Found: C, 54.22; H, 5.88 N, 14.86%.

$^1$H-NMR (DMSO) delta 1.50 to 2.20 (7H, m), 2.33 (2H, bs), 2.90 to 3.30 (5H, m), 3.49 (1H, m), 4.02 (2H, bs), 7.16 (1H, d, J=8 Hz), 7.37 (1H, s), 7.63 (1H, s), 7.74 (1H, d, J=8 Hz)), 8.63 (1H, bs), 8.00 to 9.00 (1H, bs), 10.74 (1H, bs), 11.32 (1H, bs).

EXAMPLE 6

1-[4-(2,3-Dihydro-2-oxo-1H-imidazo[4,5-b]quinolin-7-yloxy)-1-oxobutyl]-4-(1-piperidinyl)piperidine

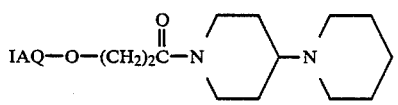

Reaction of 4-(1-piperidinyl)piperidine and -[(2,3-dihydro-2-oxo-1H-imidazo[4,5-b]quinolin-7-yl)oxo]-butyric acid (1 g) analogously to the procedure of Example 4 gave the title compound as the hydrated dihydrochloride salt, yield 1.55 g (89%), m.p. indistinct.

Anal. Calcd. for C$_{24}$H$_{31}$N$_5$O$_3$.2HCl.H$_2$O: C, 54.55: H, 6.68; N, 13.26; H$_2$O, 3.41. Found: C, 54.91: H, 6.62; N, 13.27; H$_2$O, 5.59%.

$^1$H-NMR (DMSO-d$^6$) delta: 1.20 to 1.78 (6H, m), 1.78 to 2.20 (6H, m), 2.49 (3H, m), 2.80 (2H, bs), 2.99 (1H, t, J=12 Hz), 3.30 (3H, m), 4.03 (1H, d, J=12 Hz), 4.06 (2H, t, J=6 Hz), 4.53 (1H, d, J=12 Hz), 6.37 (1H, bs), 7.19 (1H, dd, J=9 Hz, J'=2.5 Hz), 7.39 (1H, d, J=2.5 Hz), 7.62 (1H, s), 7.75 (1H, d, J=9 Hz), 10.82 (1H, bs), 11.25 (1H, s).

EXAMPLE 7

1-[4-[(2,3-Dihydro-2-oxo-1H-imidazo[4,5-b]-quinolin-7-yl)oxy]-1-oxobutyl]-4-methylpiperazine

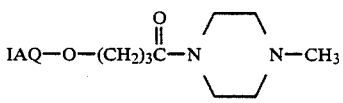

Reaction of N-methylpiperazine and 4-[(2,3-dihydro-2-oxo-1H-imidazo[4,5-b]quinolin-7-yl)oxy]butyric acid (2 g) analogously to the procedure of Example 4 gave the title compound as the hydrated dihydrochloride salt; yield 2.85 g (92%), m.p. 286°–288° C. (dec.).

Anal. Calcd. for C$_{19}$H$_{23}$N$_5$O$_3$.2 HCl. 0.4H$_2$O: C, 50.77: H, 5.79: N, 15.58: H$_2$O, 1.60. Found: C, 50.87, H, 5.65; N, 15.58: H$_2$O, 1.21%.

NMR (DMSO-d$_6$) delta 1.99 (2H, t, J=7 Hz), 2.55 (2H, t, J=7 Hz), 2.70 (3H, d, J=4 Hz), 2.80 to 3.20 (3H, m), 3.34 (2H, d, J=12 Hz), 3.49 (1H, t, J=13 Hz), 4.06 (3H, t, J=7 Hz), 4.42 (1H, d, J=13 Hz), 7.18 (1H, dd, J=9 Hz, J$^1$=2.5 Hz), 7.35 (1H, d, J=2.5 Hz), 7.60 (1H, s), 7.75 (1H, d, J=9 Hz), 11.22 (1H, d, J=10 Hz), and 11.65 (1H, bs).

EXAMPLE 8

1-[4-(2,3-Dihydro-2-oxo-1H-imidazo[4,5-b]quinolin-7-yloxy)-1-oxobutyl]-4-(2-methylpropyl)piperazine

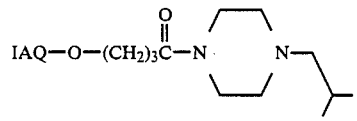

Reaction of N-(2-methylpropyl)piperazine and -[(2,3-dihydro-2-oxo-1H-imidazo[4,5-b]quinolin-7-yl)oxo]-butyric acid (1 g) analogously to the procedure of Example 4 gave the title compound as the hydrated dihydrochloride salt, yield 1.57 g (92%), m.p. 240°–243° C.

Anal. Calcd. for C$_{22}$H$_{29}$N$_5$O$_3$.2HCl.0.5H$_2$O: C, 53.56: H, 6.54; N, 14.20; H$_2$O, 1.83. Found: C, 53.45; H, 6.29: N, 14.07: H20, 7.03%.

$^1$H-NMR (DMSO-d$^6$) delta: 0.95 (6H, d, J=6.5 Hz), 1.95 to 2.15 (3H, m), 2.55 (2H, t, J=5.5 Hz), 2.87 (2H, t, J=6 Hz), 2.80 to 3.10 (2H, m), 3.30 (1H, t, J=12 Hz), 3.41 (2H, d, J=10 Hz), 3.73 (1H, t, J=12 Hz), 3.99 (1H, d, J=13 Hz), 4.06 (2H, t, J=6 Hz), 4.36 (1H, d, J=13 Hz), 7.19 (1H, dd, J=9 Hz, J'=2.5 Hz), 7.38 (1H, d, J=2.5 Hz), 7.63 (1H, s), 7.76 (1H, d, J=9 Hz), 10.92 (1H, bs) and 11.30 (1H, s).

EXAMPLE 9

1-[4-(2,3-Dihydro-2-oxo-1H-imidazo[4,5-b]quinolin-7-yloxy))-1-oxobutyl]-4-(2-ethylbutyl)piperazine

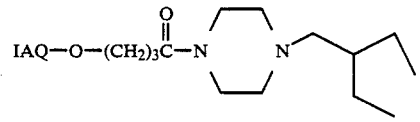

Reaction of N-[2-(ethyl)butyl]piperazine and 4-[(2,3-dihydro-2-oxo-1H-imidazo[4,5-b]quinolin-7-yl)oxo]-butyric acid (2 g) analogously to the procedure of Example 4 gave the title compound as the hydrated dihydrochloride salt, yield 3,59 g(100%), m.p. 198°–201° C.

Anal. Calcd. for C$_{24}$H$_{33}$N$_5$O$_3$.2HCl: C, 56.25: H, 6.88; N, 13.67. Found: C, 56.30: H, 7.07: N, 13.47%

$^1$H-NMR (DMSO-d$^6$) delta: 0.79 (6H, t, J-7.5 Hz), 1.25 to 1.50 (4H, m), 1.68 (1H, quintet, J=6 Hz), 1.98 (2H, quintet, J=6 Hz), 2.54 (2H, m), 2.80 to 3.10 (4H, m), 3.28 (1H, t, J=12 Hz), 3.43 (2H, d, J=10 Hz), 3.73 (1H, t, J=13 Hz), 4.04 (3H, m), 4.37 (1H, d, J=13 Hz), 4.80 (2H, bs), 7.19 (1H, dd, J=9 Hz, J'=2.5 Hz), 7.39 (1H, d, J=2 5 Hz), 7 66 (1H, s), (1H, d, J=9 Hz), 10.90 (1H, bs) and 11.39 (1H, s).

EXAMPLE 10

1-[4-(2,3-Dihydro-2-oxo-1H-imidazo[4,5-b]quinolin-7-yloxy)-1-oxobutyl]-4-(2-methoxyethyl)piperazine

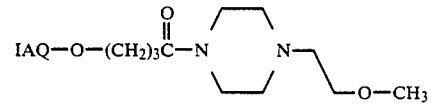

Reaction of N-(2-methoxyethyl)piperazine and 4-[(2,3-dihydro-2-oxo-1H-imidazo[4,5-b]quinolin-7-yl)oxo]butyric acid (1 g) analogously to the procedure of Example 4 gave the title compound as the hydrated dihydrochloride salt, yield 1.3 g (76%), m.p. 227°–231° C.

Anal. Calcd. for $C_{21}H_{27}N_5O_4 \cdot 2HCl \cdot 0.5H_2O$: C, 50.92: H, 6.11; N, 14.14; $H_2O$, 1.82. Found: C, 51.25: H, 6.31; N, 14.05; $H_2O$, 2.95%.

$^1$H-NMR (DMSO-$d^6$) delta: 1.98 (2H, quintet, J=6.5 Hz), 2.54 (2H, m), 2.85 to 3.20 (4H, m), 3.26 (3H, s), 3.40 to 3.70 (4H, m), 3.72 (2H, t, J=5 Hz), 4.06 (3H, m), 4.40 (1H, d, J=13 Hz), 7.17 (1H, dd, J=9hz, J'=2.5 Hz), 7.36 (1H, d, J=2.5 Hz), 7.60 (1H, s), 7.74 (1H, d, J=9 Hz), 11.24 (1H, s) and 11.36 (1H, bs).

EXAMPLE 11

1-[4-[2,3-Dihydro-2-oxo-1H-imidazo[4,5-b]-quinolin-7-yl)oxy]-1-oxobutyl]-4-phenylmethylpiperazine

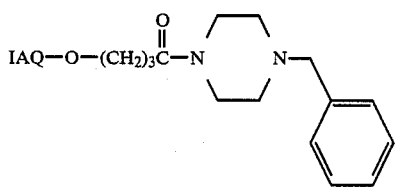

Prepared by reacting N-benzylpiperazine and 4-[(2,3-dihydro-2-oxo-1H-imidazo[4,5-b]quinolin-7-yl)oxy]-butyric acid (2 g) analogously to the procedure of Example 4. Crystallization of the crude free base from aqueous dimethylformamide gave the title compound; yield 2.12 g (68%), m.p. 267°–269° C.

Anal. Calcd for $C_{25}H_{27}N_5O_3$: C, 67.40; H, 6.11; N, 15.72. Found: C, 66.98; H, 6.14; N, 15.86%.

$^1$H-NMR (DMSO-$d^6$) delta 1.97 (2H, t, J=7 Hz), 2.27 (4H, m), 2.48 (2H, t, J=7 Hz), 3.42 (6H, bs), 4.04 (2H, t, J=7 Hz), 7.12 (1H, dd, J=9 Hz, $J^1$=2.5 Hz), 7.15 to 7.35 (6H, m), 7.49 (1H, s), 7.65 (1H, d, J=9 Hz), 10.94 (1H, s), 11.35 (1H, s).

Repeating the procedure with 5 g of 4-[(2,3-dihydro-2-oxo-1H-imidazo[4,5-b]quinolin-7-yl)oxy]butyric acid provided 7.65 g (98%) of the crude free base product. Crystallization of 3.65 g of this material from aqueous dimethylformamide gave 2.9 g of analytically pure hydrated 1-[4-[2,3-dihydro-2-oxo-1H-imidazo[4,5-b]quinolin-7-yl)oxo]-1-oxobutyl]-4-phenylmethylpiperazine.

Anal. Calcd. for $C_{25}H_{27}N_5O_3 \cdot 0.2H_2O$: C, 66.86: H, 6.15; N, 15.60: $H_2O$, 0.8. Found: C, 66.60: H, 6.19: N, 16.00; $H_2O$, 0.09%.

A 5 g sample of the free base converted to the dihydrochloride salt in methanol and triturated with methanol and diethyl ether gave the title compound as the hydrated dihydrochloride salt; yield 4.20 g (90%), m.p. 210°–216° C. (dec.).

Anal. Calcd. for $C_{25}H_{27}N_5O_3 \cdot 2HCl \cdot 0.1H_2O$: C, 57.72; H, 5.66; N, 13.47; $H_2O$, 0.35. Found: C, 58.12: H, 5.90;'N, 13.40; $H_2O$, 0.39%.

$^1$H-NMR (DMSO-$d_6$) delta 1.98 (2H, t, J=7 Hz), 2.53 (2H, m), 2.80 to 3.40 (5H, m), 3.60 (1H, t, J=12 Hz), 4.05 (3H, t, J=7 Hz), 4.28 (2H, d, J=4 Hz), 4.42 (1H, d, J=12 Hz), 7.20 (1H, dd, J=9 Hz, $J^1$=2.5 Hz), 7.41 (4H, m), 7.61 (2H, m), 7.67 (1H, s), 7.79 (1H, d, J=9 Hz), 10.19 (1H, bs), 11.39 (1H, s), 11.89 (1H, bs).

EXAMPLE 12

1-[5-[2,3-Dihydro-2-oxo-1H-imidazo[4,5-b]-quinolin-7-yl]oxy]-1-oxopentyl]-4-phenylmethylpiperazine

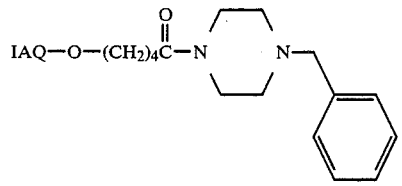

Reaction of N-benzylpiperazine and 4-[(2,3-dihydro-2-oxo-1H-imidazo[4,5-b]quinolin-7-yl)oxo]pentane acid (2 g) analogously to the procedure of Example 4 gave the title compound as the hydrated dihydrochloride salt, yield 2.7 g (76%), m.p. 190°–195° C. (dec.).

Anal. Calcd. for $C_{26}H_{29}N_5O_3 \cdot 2HCl \cdot 0.1H_2O$: C, 58.46; H, 5.89; N, 13.11, $H_2O$, 0.34. Found: C, 58.12; H, 5.91; N, 12.84%.

$^1$H-NMR (DMSO-$d^6$) delta: 1.55 to 1.85 (4H, m), 2.42 (2H, m), 2.75 to 3.30 (5H, m), 3.60 (1H, t, J=12 Hz), 4.04 (3H, m), 4.31 (2H, m), 4.41 (1H, d, J=13 Hz), 7.20 (1H, dd, J=9 Hz, J'=2.5 Hz), 7.41 (4H, m), 7.26 (2H, m), 7.69 (1H, s), 7.82 (1H, d, J=9 Hz), 11.45 (1H, s) and 11.94 (1H, bs).

EXAMPLE 13

1-[4-(2,3-Dihydro-2-oxo-1H-imidazo-(4,5-b)quinolin-7-yloxy)-1-oxobutyl]-4-[(4-fluorophenyl)methyl-piperazine

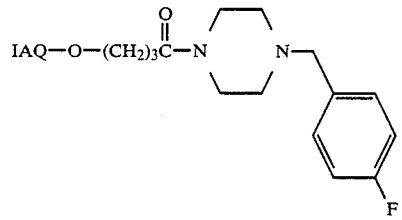

Reaction of N-(4-fluorobenzyl)piperazine and 4-[(2,3dihydro-2-oxo-1H-imidazo[4,5-b]quinolin-7-yl)oxy]butyric acid (2 g) analogously to the procedure of Example 4 gave the title compound as the diethyl ether solvated hydrated dihydrochloride salt; yield 4.00 g (100%), m.p. indistinct-decomposed at 200°–220° C.

Anal. Calcd. for $C_{25}H_{26}FN_5O_3 \cdot 2HCl \cdot 0.2H_2O \cdot 0.4 C_4H_{10}O$: C, 56.09; H, 5.74; N, 12.30; $H_2O$, 0.63. Found: C, 55.83; H, 6.36; N, 12.73; $H_2O$, 0.75%.

H-NMR (DMSO-$d^6$) delta 1.03 (1.2H, t, J=7 Hz), 1.97 (2H, quintet, J=6 Hz), 2.52 (2H, m), 2.80 to 3.30 (5H, m), 3.34 (0.8H, q, J=7 Hz), 3.59 (1H, t, J=12 Hz), 4.03 (3H, t, J=7 Hz), 4.31 (2H, bs), 4.42 (1H, d, J=15 Hz), 5.60 (1H, bs), 7.20 (3H, m), 7.38 (1H, d, J=2.5 Hz), 7.69 (3H, m), 7.99 (1H, d, J=9 Hz), 11.49 (1H, s, N$\underline{H}$), 11.93 (1H, bs).

EXAMPLE 14

1-[4-(2,3-Dihydro-2-oxo-1H-imidazo[4,5-b]quinolin-7-(yloxy)-1-oxobutyl]-4-[[3-trifluormethyl)phenyl-]methyl]piperazine

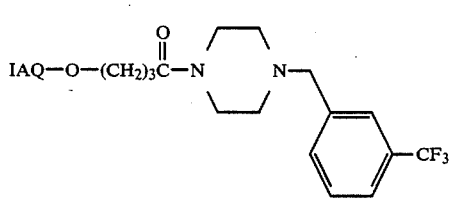

Reaction of N-[3-(trifluoromethyl)benzyl]piperazine and 4-[(2,3-dihydro-2-oxo-1H-imidazo[4,5-b]-quinolin-7-yl)oxy]butyric acid (2 g) analogously to the procedure of Example 4 gave the title compound after crystallization from methanol/diethyl ether as the hydrated dihydrochloride salt; yield 3.32 g (83%), m.p. 198°–208° C.

Anal Calcd for $C_{26}H_{26}F_3N_5O_3 2HCl$ 0.5 $H_2O$: C, 52.45: H, 4.91; N, 11.77: $H_2O$, 1.51. Found: C, 52.83; H, 5.24; N, 11.39; $H_2O$, 0.76%.

$^1$H-NMR (DMSO-$d^6$) delta 1.98 (2H, quintet, J=7 Hz), 2.53 (2H, m,), 2.80 to 3.40 (5H, m), 3.60 (1H, t, J=15 Hz), 4.05 (3H, t, J=6 Hz), 4.44 (3H, bs), 7.19 (1H, dd, J=9 Hz, J$^1$=2.5 Hz), 7.39 (1H, d, J=2.5 Hz), 7.65 (1H, s), 7.60 to 7.80 (3H, m), 7.95 (1H, d, J=9 Hz), 8.13 (1H, s), 11.37 (1H, s), 11.70 (1H, s), 12.13 (1H, bs).

EXAMPLE 15

1-[4-(2,3-Dihydro-2-oxo-1H-imidazo[4,5-b]quinolin-7-yloxy)-1-oxobutyl]-4-(4-methoxyphenyl)methyl]piperazine

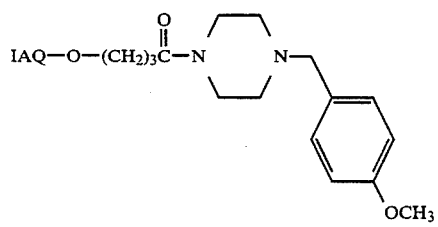

Reaction of N-(4-methoxy)benzyl)piperazine and -[(2,3-dihydro-2-oxo-1H-imidazo[4,5-b]quinolin-7-yl)oxy]butyric acid (2 g) analogously to the procedure of Example 4 gave the title compound after crystallization from methanol/diethyl ether as the hydrated dihydrochloride salt; yield 3.02 g (79%), m.p. 200°–207° C.

Anal. Calcd. for $C_{26}H_{29}N_5O_4.2HCl.0.5$ $H_2O$: C, 56.02: H, 5.79; N, 12.57; $H_2O$, 1.62. Found: C, 56.32: H, 6.44; N, 12.61; $H_2O$, 1.66%.

$^1$H-NMR (DMSO-$d^6$) delta 1.98 (2H, m), 2.24 (2H, m), 2.80 to 3.30 (5H, m), 3.58 (1H, t, J=12 Hz), 3.74 (3H, s), 4.05 (3H, bs), 4.32 (2H, bs), 4.43 (1H, d, J=12 Hz), 6.95 (2H, d, J=6 Hz), 7.20 (1H, d, J=9 Hz), 7.39 (1H, s), 7.52 (2H, d, J=6 Hz), 7.68 (1H, s), 7.79 (1H, d, J=9 Hz).

EXAMPLE 16

1-[4-(2,3-Dihydro-2-oxo-1H-imidazo[4,5-b]quinolin-7-yloxy)-1-oxobutyl]-4-(2-thienylmethyl)piperazine

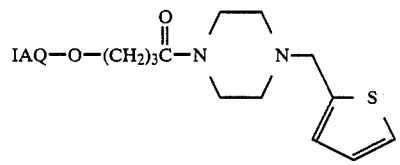

Reaction of N-(2-thienylmethyl)piperazine and 4-[(2,3-dihydro-2-oxo-1H-imidazo[4,5-b]quinolin-7-yl)oxy]butyric acid (2 g) analogously to the procedure of Example 4 gave the title compound after suspending in methanol as the dihydrochloride salt; yield 3.50 g (95%), m.p. 244°–245° C. (dec).

Anal. Calcd. for $C_{23}H_{25}N_5O_3S.2HCl$: C, 52.68; H, 5.19; N, 13.36. Found: C, 52.69; H, 5.51; N, 13.06%.

$^1$H-NMR (DMSO-$d^6$) delta 1.97 (2H, quintet, J=6 Hz), 2.52 (2H, m), 2.80 to 3.40 (5H, m), 3.58 (1H, t, J=12 Hz), 4.05 (3H, t, J=6 Hz), 4.44 (1H, d, J=12 Hz), 4.53 (2H, bs), 710 (1H, dd, J=2.5 Hz), 7.20 (1H, dd, J=9 Hz, J$^1$=2.5 Hz), 7.40 (2H, m), 7.66 (2H, m), 7.81 (1H, d, J=9 Hz), 11.42 (1H, s), 11.80 (1H, bs), 12.04 (1H, bs).

EXAMPLE 17

1-[4-(2,3-Dihydro-2-oxo-1H-imidazo[4,5-b]quinolin-7-yloxy)-1-oxobutyl]-4-(3-thienylmethyl)piperazine

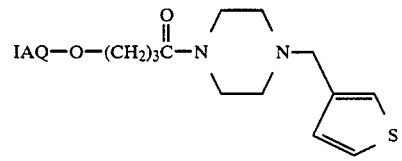

Reaction of N-(3-thienylmethyl)piperazine and 4-[(2,3-dihydro-2-oxo-1H-imidazo[4,5-b]quinolin-7-yl)oxy]butyric acid (2g) analogously to the procedure of Example 4 gave the title compound after crystallization from methanol/diethyl ether as the dihydrochloride salt; yield 3.35 g (91%), m.p. indistinct, decomposed at 245°–250° C.

Anal. Calcd. for $C_{23}H_{25}N_5O_3S.2HCl$: C, 52.68; H, 5.19; N, 13.36. Found: C, 52.83; H, 5.53; N, 13.47%.

$^1$H-NMR (DMSO-$d_6$) delta 1.98 (2H, quintet, J=6 Hz), 2.54 (2H, m), 2.70 to 3.10 (2H, m), 3.13 (1H, t, J=13 Hz), 3.23 (3H, bs), 3.59 (1H, t, J=13 Hz), 4.06 (3H, t, J=6 Hz), 4.30 (2H, d, J=4 Hz), 4.42 (1H, d, J=13 Hz), 7.19 (1H, dd, J=9Hz, J$^1$=2.5 Hz), 7.39 (2H, m), 7.62 (2H, m), 7.77 (2H, m), 9.88 (1H, bs), 11.34 (1H, s), 11.95 (1H, bs).

EXAMPLE 18

1-[4-(2,3-Dihydro-2-oxo-1H-imidazo[4,5-b] quinolin-7-yloxy)-1-oxobutyl]-4[tetrahydro-1H-Dyran-2-yl)-ethyl]Deuerazne:

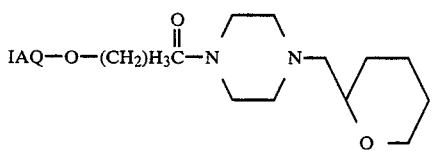

Reaction of N-[(tetrahydro-2H-pyran-2-yl)methyl]-piperazine and 4-[(2,3-dihydro-2-oxo-1H-imidazo[4,5-b]-quinolin-7-yl)oxo]butyric acid (1 g) analogously to the procedure of Example 4 gave the title compound as the hydrated dihydrochloride salt, yield 1.33 g (73%), m.p. [222°–232° C.

Anal. Calcd. for $C_{24}H_{31}N_5O_4.2HCl.H_2O$: C, 52.95; H, 6.48: N, 12.87; $H_2O$, 3.31. Found: C, 53.28: H, 6.44; N, 12.73: $H_2O$, 9.68%.

$^1$H-NMR (DMSO-$d^6$) delta: 1.30 to 1.60 (4H, m), 1.98 (2H, t, J=6.5Hz), 2.54 (2H, m), 2.80 to 3.30 (5H, m), 3.35 to 3.70 (4H, m), 3.83 (2H, d, J=10Hz), 4.06 (2H, t, J=6Hz), 3.95 to 4.05 (1H, m), 4.37 (1H, m), 6.57 (1H, b), 7.18 (1H, dd, J=9Hz, J'=2.5Hz), 7.37 (1H, d, J=2.5Hz), 7.61 (1H, s), (1H, d, J=9Hz), 11.10 (1H, bs) and 11.27 (1H, s).

EXAMPLE 19

1-[4-(2,3-Dihydro-2-oxo-1-imidazo[4,5-b]-quinolin-7-yloxy)-1-oxobutyl]-4-(2-pyridinyl)piperazine

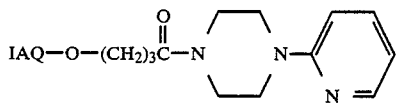

Reaction of 1-(2-pyridinyl)piperazine and [(2,3-dihydro-2-oxo-1H-imidazo[4,5-b]quinolin-7-yl)oxy]butyric acid (2g) analogously to the procedure of Example 4 gave the title compound as the hydrated hydrochloride salt yield 3.38 g (96%), m.p. 195°–200° C. (dec.).

Anal. Calcd. for $C_{23}H_{24}N_6O_3.2HCl.H_2O$: C, 52.78; H, 5.40; N, 16.06; $H_2O$, 3.44. Found: C, 52.49; H, 5.96; N, 15.45: $H_2O$, 2.65%.

$^1$H-NMR (DMSO-$d^6$) delta 1.99 (2H, t, J=6Hz), 2.55 (2H, t, J=6Hz), 3.50 to 3.95 (4H, m), 4.07 (2H, t, J=6Hz), (1H, t, J=6.5Hz), 7.18 (1H, dd, J=9Hz, J$^1$=2.5 Hz), 7.35 (2H, m), 7.64 (1H, s), 7.76 (1H, d, J=9Hz), 8.00 (2H, m), 11.35 (1H, s).

EXAMPLE 20

1-[4-[(2,3-Dihydro-2-oxo-1H-imidazo[4,5-b]quinolin-7-yl)oxy]-1-oxobutyl]-4-(2-pyrimidinyl)piperazine

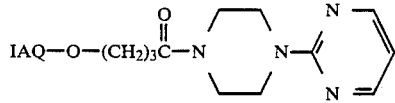

Reaction of N-(2-pyrimidinyl)piperazine and 4-[(2,3-dihydro-2-oxo-1H-imidazo[4,5-b]quinolin-7-yl)oxy]-butyric acid (2 g) analogously to the procedure of Example 4 gave the title compound as the hydrated dihydrochloride salt; yield 3.67 g (100%), m.p. 184°–187° C.

Anal. Calcd. for $C_{22}H_{23}N_7O_3.2HCl.H_2O$: C, 50,39: H, 5.20; N, 18.70: $H_2O$ 3.44. Found: C, 50.54 H, 5.08: N, 18.55: $H_2O$, 3.24%.

$^1$H-NMR (DMSO-$d^6$) delta 2.01 (2H, t, J=6Hz), 2.38 (s,), 2.56 (2H, t, J=6Hz), 3.58 (4H, s), 3.78 (4H, 2s), 4.08 (2H, t, J=6Hz), 6.78 (1H, t, J=5Hz), 7.24 (2H, d, J=9Hz), 7.43 (1H, s), 7.72 (1H, s), 7,84 (1H, d, J=9Hz), 8.46 (2H, d, J=5Hz), 8.96 (2H, bs), 11.51 (1H, s).

EXAMPLE 21

1-(Cyclopentylmethyl)-4-[4-(2,3-dihydro-2-oxo-1-H-imidazo[4,5-b]quinolin-7-yloxy)-1-oxobutyl-piperazine

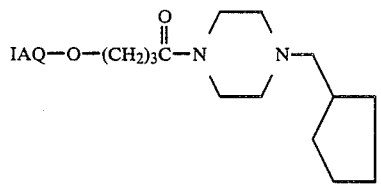

Reaction of N-cyclopentylmethyl)piperazine and 4-[(2,3-dihydro-2-oxo-1H-imidazo[4,5-b]quinolin-7-yl)oxo]butyric acid (2 g) analogously to the procedure of Example 4 gave the title compound as the hydrated dihydrochloride salt, yield 3.0 g (84%), m.p. 244°–250° C.

Anal. Calcd. for $C_{24}H_{31}N_5O_3.2HCl.0.8H_2O$: C, 54.93; H, 6.65; N, 13.35: $H_2O$, 2.75. Found: C, 55.19: H, 6.64: N, 13.42: $H_2O$, 7.11%.

1H-NMR (DMSO-$d^6$) delta: 1.99 (2H, t, J=6.5 Hz), (1H, sextuplet, J=7.5 Hz), 2.54 (2H, m), 2.70 to 3.10 (4H, m), 3.21 (1H, t, J=13 Hz), 3.43 (2H, m), 3.66 (1H, t, J=12 Hz), 3.95 to 4.05 (1H, m), 4.06 (2H, t, J=6 Hz), 4.39 (1H, d, J=13 Hz), 7.18 (1H, dd, J=6 Hz, J'=2.5 Hz), 7.37 (1H, d, J=2.5 Hz), 7.60 (1H, s), 7.74 (1H, d, J=9 Hz), 11.04 (1H, bs) and 11.22 (1H, s).

EXAMPLE 22

1-(Cyclohexylmethyl)-4-[4-(2,3-dihydro-2-oxo-1H-imidazo[4,5-b]quinolin-7-yloxy)-1-oxybutyl]piperazine

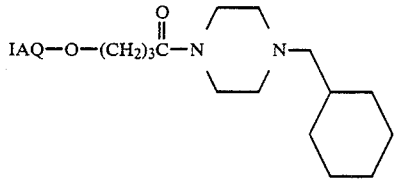

Reaction of N-(cyclohexylmethyl)piperazine and 4-[(2,3-dihydro-2-oxo-1H-imidazo[4,5-b]quinolin-7-yl)oxy]butyric acid (2 g) analogously to the procedure of Example 4 gave the title compound after crystallization from methanol/diethyl ether as the hydrated dihydrochloride salt; yield 3.75 g (100%), m.p. 258°–260° C. (dec).

Anal. Calcd. for $C_{25}H_{33}N_5O_3.2HCl.0.4 H_2O$: C, 56.48; H, 6.79: N, 13.18; $H_2O$, 1.36. Found: C, 56.72: H, 7.47; N, 12.47; H20, 0.35%.

$^1$H-NMR (DMSO-$d^6$) delta 0.93 (2H, q, J=11 Hz), 1.15 (3H, m), 1.50 to 1.95 (6H, m), 2.01 (2H, t, J=6 Hz), 2.58 (2H, m), 2.90 to 3.20 (4H, m), 3.33 (1H, t, J=12 Hz), 3.44 (2H, bs), 3.77 (1H, t, J=12 Hz), 4.08 (3H, t, J=6 Hz), 4.39 (1H, d, J=12 Hz), 7.24 (1H, dd, J=9 Hz, J$^1$=2.5 Hz), 7.44 (1H, dd, J=2.5 Hz), 7.72 (1H, s), 7.84 (1H, d, J=9 Hz), 11.13 (1H, bs), 11.50 (2H, bs).

EXAMPLE 23

1-(Cyclohexylmethyl)-4-[5-(2,3-dihydro-2-oxo-1H-imidazo-[4,5-b]quinolin-7-yloxy)-1-oxopentyl]-piperazine

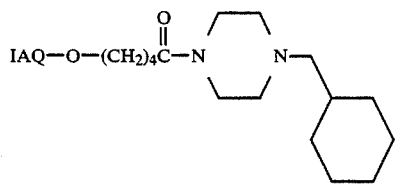

Reaction of N-(cyclohexylmethyl)piperazine and 4-[(2,3-dihydro-2-oxo-1H-imidazo[4,5-b]quinolin-7-yl)oxo]pentanoic acid (2 g) analogously to the procedure of Example 4 gave the title compound as the hydrated dihydrochloride salt, yield 3.15 g (88%), m.p. indistinct.

Anal. Calcd. for $C_{26}H_{35}N_5O_3.2HCl.0.8H_2O$: C, 56.48; H, 7.04; N, 12.67; $H_2O$, 2.61. Found: C, 56.41; H, 6.87; N, 12.52: $H_2O$, 2.32%.

$^1$H-NMR (DMSO-d$^6$) delta: 0.93 (2H, m), 1.00 to 1.40 (4H, m), 1.50 to 1.95 (9H, m), 2.44 (2H, m), 2.90 (4H, m), 3.24 (1H, t, J=12 Hz), 3.42 (2H, d, J=10 Hz), 3.69 (1H, t, J=13 Hz), 4.04 (3H, m), 4.35 (1H, d, J=13 Hz), 6.09 (2H, bs), 7.17 (1H, d, J=9 Hz), 7.38 (1H, s), 7.61 (1H, s), 7.75 (1H, d, J=9 Hz), 10.87 (1H, bs) and 11.26 (1H, s).

EXAMPLE 24

1-(Cyclohexylmethyl)-4-[6-(2,3-dihydro-2-oxo-1H-imidazo[4,5-b]quinolin-7-yloxy)-1-oxohexyl]piperazine

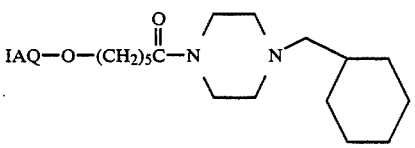

Reaction of N-(cyclohexylmethyl)piperazine and 5-[(2,3-dihydro-2-oxo-1H-imidazo[4,5-b]quinolin-7-yl)oxo]hexanoic acid (1.5 g) analogously to the procedures of Example 4 gave the title compound as the hydrated dihydrochloride salt, yield 2.62 g (100%), m.p. 290°–292° (dec.).

Anal. Calcd. for $C_{27}H_{37}N_5O_3.0.7H_2O$: C, 57.39; H, 7.21; N, 12.40: $H_2O$, 2.23. Found: C, 57.25; H, 7.22: N, 13.23, $H_2O$, 3.26%.

$^1$H-NMR (DMSO-D$^6$) delta: 0.90 (2H, q, J=11 Hz), 0.97 to 1.30 (3H, m), 1.30 to 1.90 (14H, m), 3.37 (2H, t, J=7 Hz), 2.75 to 3.10 (4H, m), 3.24 (1H, t, J=12 Hz), 3.42 (2H, m), 3.69 (1H, t, J=12 Hz), 4.02 (3H, t, J=6 Hz), 4.34 (1H, d, J=14 Hz), 6.19 (1H, bs), 7.17 (1H, dd, J=9 Hz, J$^1$=2.5 Hz), 7.38 (1H, d, J=2.5 Hz), 7.63 (1H, s), 7.75 (1H, d, J=9 Hz), 10.92 (1H, bs) and 11.30 (1H, s).

EXAMPLE 25

1-Cycloheptanyl-4-[4-(2,3-dihydro-2-oxo-1H-imidazo[4,5-b]quinolin-7-yloxy)-1-oxobutyl]piperazine

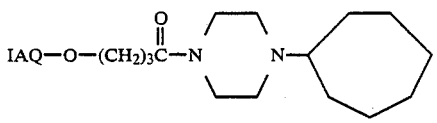

Reaction of N-(cycloheptanyl)piperazine and 4-[(2,3-dihydro-2-oxo-1H-imidazo[4,5-b]quinolin-7-yl)oxy]butyric acid (2 g) analogously to the procedure of Example 4 gave the title compound after crystallization from methanol/diethyl ether as the hydrated dihydrochloride salt; yield 2.78 g (76%), m.p. 210°–225° C.

Anal. Calcd. for $C_{25}H_{33}N_5O_3$ 2HCl 0.4 $H_2O$: C, 56.48; H, 6.79; N, 13.18; $H_2O$, 1.36. Found: C, 56.67; H, 7.05; N, 12.97: $H_2O$, 1.14%.

$^1$H-NMR (DMSO-d$^6$) delta 1.30 to 1.80 (10H, m), 2.00 (3H, m), 2.55 (3H, m), 2.80 to 3.40 (5H, m), 3.65 (1H, t, J=12 Hz), 4.04 (3H, m), 4.00 (bs), 4.47 (1H, d, J=12 Hz), 7.18 (1H, dd, J=9 Hz, J$^1$=2.5 Hz), 7.36 (1H, d, J=2.5 Hz), 7.58 (1H, s), 7.72 (1H, d, J=9 Hz), 11.10 (1H, bs).

EXAMPLE 26

1-[4-[2,3-Dihydro-1-methyl-2-oxo-1H-imidazo[4,5-b]-quinolin-1-yl)oxy]-1-oxobutyl]-4-phenylmethyl-piperazine

Reaction of N-benzylpiperazine and 4-[(2,3-dihydro-1-methyl-2-oxo-1H-imidazo[4,5-b]quinolin-7-yl)oxo]butyric acid (1.5 g) analogously to the procedure of Example 4 gave the title compound as the hydrated dihydrochloride salt, yield 2.2 g (83%), m.p. indistinct.

Anal. Calcd. for $C_{26}H_{29}N_5O_3.2HCl.0.5H_2O$: C, 57.68; H, 5.96; N, 12.94; $H_2O$, 1.66. Found: C, 57.73; H, 6.50: N, 12.61; $H_2O$, 1.03%.

$^1$H-NMR (DMSO-d$^6$) delta: 1.98 (2H, q, J=6 Hz), 2.50 (2H, m), 2.80 to 3.40 (5H, m), 3.32 (3H, s). 3.61 (1H, t, J=12 Hz), 4.06 (3H, t, J=7 Hz), 4.28 (2H, d, J-4 Hz), 4.42 (1H, d, J=13 Hz), 7.18 (1H, dd, J=9 Hz, J$^1$=2.5 Hz), 7.29 (1H, d, J=2.5 Hz), 7.40 (3H, m), 7.60 (2H, m), 7.70 (1H, s), 7.79 (1H, d, J=9 Hz), 11.91 (1H, bs).

EXAMPLE 27

1-(Cyclohexylmethyl)-4-[4-(2,3-dihydro-1-methyl-2-oxo-1H-imidazo[4,5-b]quinolin-7-yloxy)-1-oxobutyl]-piperazine

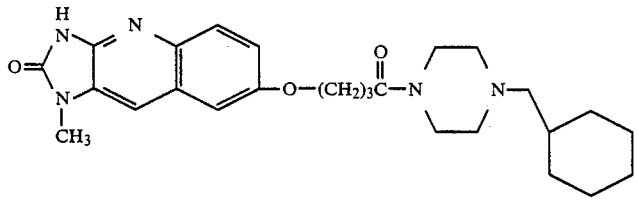

Reaction of N-(cyclohexylmethyl)piperazine and 4-[(2,3-dihydro-1-methyl-2-oxo-1H-imidazo[4,5-b]quinolin-7yl)oxo]butyric acid (0.4 g) analogously to the procedure of Example 4 gave the title compound as the hydrated dihydrochloride salt, yield 0.71 g (100%), m.p. indistinct.

Anal. Calcd. for $C_{26}H_{35}N_5O_3 \cdot 2HCl \cdot 0.7H_2O$: C, 56.67; H, 7.03; N, 12.71; $H_2O$, 2.29. Found: C, 57.23 H, 7.14; N, 12.01; $H_2O$, 2.52.

$^1$H-NMR (DMSO-$d^6$) delta: 0.94 (2H, q, J=11 Hz), 1.15 (3H, m), 1.55 to 1.90 (6H, m), 2.00 (2H, t, J=6.5 Hz), 2.56 (2H, m), 2.80 to 3.05 (4H, m), 3.19 (1H, t, J=11.5 Hz), 3.33 (3H, s), 3.44 (2H, m), 3.63 (1H, t, J=11.5 Hz), 3.80 (bs), 3.90 to 4.15 (4H, t, J=6 Hz), 4.38 (1H, d, J=13 Hz), 7.17 (1H, dd, J=9 Hz, $J^1$=2.5 Hz), 7.30 (1H, d, J=2.5 Hz), 7.66 (1H, s), 7.71 (1H, d, J=9 Hz) and 10.42 (1H, bs).

What is claimed is:

1. A compound of the formula

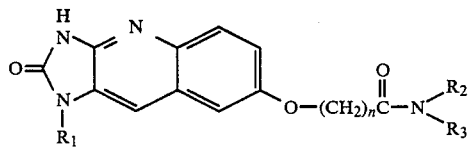

wherein
n is 3 to 5;
$R_1$ is alkyl of 1 to 4 carbon atoms;
$R_2$ is hydrogen:
$R_3$ is 1-piperidinylethyl, 1-benzylpiperidin-4-yl, 4-(1-piperidinyl)piperidine, (1-alkyl-2pyrrolidinyl)alkyl where alkyl is 1 to 4 carbon atoms, 3-quinuclidinyl:
$R_2$ and $R_3$ together with the nitrogen atom to which they are attached form 4-$R_4$-piperazin-1-yl wherein $R_4$ is alkyl of 1 to 7 carbon atoms, alkoxyethyl of 3 to 7 carbon atoms, pyridinyl, pyrimidinyl, tetrahydropyranylmethyl, thienylmethyl, cycloalkyl($CH_2$)$_m$ where m is zero or one and cycloalkyl is 5 to 7 carbon atoms except m is zero when cycloalkyl is 7 carbon atoms, benzyl, 4-fluorobenzyl, 3-trifluoromethylbenzyl, 4-alkoxybenzyl where alkoxy is 1 to 4 carbon atoms:
or a pharmaceutically acceptable salt thereof.

2. The compound of claim 1 wherein $R_1$ is hydrogen.

3. The compound of claim 1 wherein $R_1$ is hydrogen and $R_3$ and $R_3$ together with the nitrogen to which they are attached form 4-$R_4$-piperazin-1-yl.

4. The compound of claim 3 wherein $R_4$ is cycloalkyl-($CH_2$)$_m$ wherein m is zero or one and cycloalkyl is 5-7 carbon atoms except m is zero when cycloalkyl is 7 carbon atoms.

5. The compound of claim 1 or a pharmaceutically acceptable salt thereof which is 4-[2,3-dihydro-2-oxo-1H-imidazo[4,5-b]quinolin-7-yl)-oxy]-N-[2-(1-piperidinyl)ethyl]butanamide.

6. The compound of claim 1 or a pharmaceutically acceptable salt thereof which is 4-[(2,3-dihydro-2-oxo-1H-imidazo[4,5-b]quinolin-7-yl)oxy]-N-[(1-ethyl-2pyrrolidinyl)methyl]butanamide.

7. The compound of claim 1 or a pharmaceutically acceptable salt thereof which is 4-[2,3-dihydro-2-oxo-1H-imidazo[4,5-b]-quinolin-7-yl)oxo]-N-[2-(1-methyl-2-pyrrolidinyl)ethyl]butanamide.

8. The compound of claim 1 or a pharmaceutically acceptable salt thereof which is 4-(2,3-dihydro-1-oxo-1H-imidazo [4,5-b]-quinolin-7-yloxy)-N-[1-(phenylmethyl)-4-piperidinyl)butanamide.

9. The compound of claim 1 or a pharmaceutically acceptable salt thereof which is N-(1-azabicyclo[2.2.2]oct3-yl)-4-[2,3-dihydro-2-oxo-1H-imidazo[4,5-b]-quinolin-7-yl)oxy]butanamide.

10. The compound of claim 1 or a pharmaceutically acceptable salt thereof which is 1-[4-(2,3-dihydro-2-oxo-1H-imidazo[4,5-b]quinolin-7-yloxy)-1-oxobutyl]-4-(1piperidinyl)piperidine.

11. The compound of claim 1 or a pharmaceutically acceptable salt thereof which is 1-[4-[(2,3-dihydro-2-oxo-1H-imidazo-[4,5-b]quinolin-7-yl)oxy]-1-oxobutyl]-4methylpiperazine.

12. The compound of claim 1 or a pharmaceutically acceptable salt thereof which is 1-[4-(2,3-dihydro-2-oxo-1Himidazo[4,5-b]quinolin-7-yloxy)-1-oxobutyl]-4-(2-methylpropyl)piperazine.

13. The compound of claim 1 or a pharmaceutically acceptable salt thereof which is 1-[4-(2,3-dihydro-2-oxo-1Himidazo[4,5-b]quinolin-7-yloxy)-1-oxobutyl]-4-(2-methoxyethyl)piperazine.

14. The compound of claim 1 or a pharmaceutically acceptable salt thereof which is 1-[4-[2,3-dihydro-2-oxo-1Himidazo[4,5-b]-quinolin-7-yl)oxy]-1-oxobutyl]-4-phenylmethylpiperazine.

15. The compound of claim 1 or a pharmaceutically acceptable salt thereof which is 1-[5-[2,3-dihydro-2-oxo-1Himidazo[4,5-b]-quinolin-7-yl]oxy]-1-oxopentyl]-4-phenylmethylpiperazine.

16. The compound of claim 1 or a pharmaceutically acceptable salt thereof which is 1-[4-(2,3-dihydro-2-oxo-1H-imidazo-(4,5-b)quinolin-7-yloxy)-1-oxobutyl]-4-[(4-fluorophenyl)methyl]-piperazine.

17. The compound of claim 1 or a pharmaceutically acceptable salt thereof which is 1-[4-(2,3-dihydro-2-oxo-1H-imidazo[4,5-b]-quinolin-7-yloxy)-1-oxobutyl]-4-[[3-(trifluoro-methyl)phenyl]methyl]piperazine.

18. The compound of claim 1 or a pharmaceutically acceptable salt thereof which is 1-[4-(2,3-dihydro-2-oxo-1H-imidazo[4,5-b]-quinolin-7-yloxy)-1-oxobutyl]-4-(4methoxyphenyl)methyl]piperazine.

19. The compound of claim 1 or a pharmaceutically acceptable salt thereof which is 1-[4-(2,3-dihydro-2- oxo-1H-imidazo[4,5-b]-quinolin-7-yloxy)-1-oxobutyl]-4-(2thienylmethyl)piperazine.

20. The compound of claim 1 or a pharmaceutically acceptable salt thereof which is 1-[4-(2,3-dihydro-2-oxo-1-H-imidazo[4,5-b]-quinolin-7-yloxy)-1-oxobutyl]-4-(3-thienylmethyl)piperazine.

21. The compound of claim 1 or a pharmaceutically acceptable salt thereof which is 1-[4-(2,3-dihydro-2-oxo-1-H-imidazo[4,5-b]quinolin-7-yloxy)-1-oxobutyl]-4-[tetrahydro-1H-pyran-2-yl)-ethyl]piperazine.

22. The compound of claim 1 or a pharmaceutically acceptable salt thereof which is 1-[4-(2,3-dihydro-2-oxo-1-imidazo-[4,5-b]quinolin-7-yloxy)-1-oxobutyl]-4-(2pyridinyl)piperazine.

23. The compound of claim 1 or a pharmaceutically acceptable salt thereof which is 1-[4-[(2,3-dihydro-2-oxo-1H-imidazo[4,5-b]-quinolin-7-yl)oxy]-1-oxobutyl]-4-(2pyrimidinyl)piperazine.

24. The compound of claim 1 or a pharmaceutically acceptable salt thereof which is 1-(cyclopentylmethyl)-4[4-(2,3-dihydro-2-oxo-1H-imidazo[4,5-b]quinolin-7-yloxy)-1-oxobutyl-piperazine.

25. The compound of claim 1 or a pharmaceutically acceptable salt thereof which is 1-(cyclohexylmethyl)-4[4-(2,3-dihydro-2-oxo-1H-imidazo[4,5-b]quinolin-7-yloxy)-1-oxybutyl]piperazine.

26. The compound of claim 1 or a pharmaceutically acceptable salt thereof which is 1-(cyclohexylmethyl)-4-[5-(2,3-dihydro-2-oxo-1H-imidazo[4,5-b]quinolin-7-yloxy)-1-oxopentyl]-piperazine.

27. The compound of claim 1 or a pharmaceutically acceptable salt thereof which is 1-cycloheptanyl-4-[4-(2,3-dihydro-2-oxo-1H-imidazo[4,5-b]quinolin-7-yloxy)-1-oxobutyl]piperazine.

28. The compound of claim 1 or a pharmaceutically acceptable salt thereof which is 1-[4-(2,3-dihydro-2-oxo-1H-imidazo[4,5-b]quinolin-7-yloxy)-1-oxobutyl]-4-[(2-ethyl)butyl]piperazine.

29. The compound of claim 1 or a pharmaceutically acceptable salt thereof which is 1-(cyclohexylmethyl)-4-[6-(2,3-dihydro-2-oxo-1H-imidazo[4,5-b]quinolin-7-yloxy)-1-oxohexyl]piperazine.

30. The compound of claim 1 or a pharmaceutically acceptable salt thereof which is 1-[4-[2,3-dihydro-1-methyl-2-oxo-1H-imidazo[4,5-b]-quinolin-1-yl)oxy]-1-oxobutyl]-4-phenylmethyl-piperazine.

31. The compound of claim 1 or a pharmaceutically acceptable salt thereof which is 1-(cyclohexylmethyl)-4-[4-(2,3-dihydro-1-methyl-2-oxo-1H-imidazo[4,5-b]quinolin-7-yloxy)-1-oxobutyl]piperazine.

32. A method for inhibiting cyclic AMP phosphodiesterase in a mammal which comprises administering a therapeutically effective amount of a compound of claim 1 or a pharmaceutically acceptable salt thereof.

33. A method for increasing heart inotropic activity which comprises administering to a warm blooded animal, in need of such treatment a therapeutically effective amount of a compound of claim 1 or a pharmaceutically acceptable salt thereof.

34. The pharmaceutical composition for inhibiting cyclic AMP phosphodiesterase comprising a therapeutically effective amount of a compound of claim 1 or a pharmaceutically acceptable acid addition salt thereof and a pharmaceutical carrier.

35. A method for inhibiting blood platelet aggregation in a mammal which comprises administering a therapeutically effective amount of a compound of claim 1 or a pharmaceutically acceptable salt thereof.

36. The pharmaceutical composition for inhibiting blood platelet aggregation comprising a therapeutically effective amount of a compound of claim 1 or a pharmaceutically acceptable acid addition salt thereof and a pharmaceutical carrier.

37. The pharmaceutical composition for increasing heart inotropic activity comprising a therapeutically effective amount of a compound of claim 1 or a pharmaceutically acceptable acid addition salt thereof and a pharmaceutical carrier.

* * * * *

UNITED STATES PATENT AND TRADEMARK OFFICE
CERTIFICATE OF CORRECTION

PATENT NO. : 4,943,573
DATED : July 24, 1990
INVENTOR(S) : Nicholas A. Meanwell

It is certified that error appears in the above—identified patent and that said Letters Patent is hereby corrected as shown below:

Column 13, first formula, that portion reading "$(CH_2)_2$" should read -- $(CH_2)_3$ --.
Column 23, line 63, "$R_3$ and $R_3$" should read -- $R_2$ and $R_3$ --.
Column 24, line 29, "oct3" should read -- oct-3 --; line 34, "(1piperidinyl)" should read -- (1-piperidinyl) --; line 38, "4methyl" should read -- 4-methyl --; line 41, "1Himidazo" should read -- 1H-imidazo --; line 45, "1Himidazo" should read -- 1H-imidazo --; line 49, "1Himidazo" should read -- 1H-imidazo --; line 53, "1Himidazo" should read -- 1H-imidazo --; line 66, "(4methoxyphenyl)" should read -- (4-methoxyphenyl) --.
Column 25, line 2, "(2thienylmethyl)" should read -- (2-thienylmethyl) --; line 5, "oxo-1-H-imidazo" should read -- oxo-1H-imidazo --; line 9, "oxo-1-H-imidazo" should read -- oxo-1H-imidazo --; line 14, "(2pyridinyl)" should read -- (2-pyridinyl) --; line 18, "4-(2pyrimidinyl)" should read -- 4-(2-pyrimidinyl) --; line 21, "4[4-" should read -- 4-[4- --; line 25, "4[4-" should read -- 4-[4- --.

Signed and Sealed this

Sixteenth Day of April, 1991

Attest:

HARRY F. MANBECK, JR.

Attesting Officer

Commissioner of Patents and Trademarks